United States Patent [19]

Bost

[11] 3,963,571

[45] June 15, 1976

[54] OXIDATION OF HYDROXY ACIDS PRODUCED FROM BACTERIAL OXIDATION OF PARAFFINS

[75] Inventor: Howard W. Bost, Bartlesville, Okla.

[73] Assignee: Phillips Petroleum Company, Bartlesville, Okla.

[22] Filed: Apr. 10, 1974

[21] Appl. No.: 459,623

[52] U.S. Cl............................................ 195/28 R
[51] Int. Cl.² ........................................ C12B 1/00
[58] Field of Search .............. 195/28 R; 260/586 A, 260/586 R, 537 P, 531 R, 485 R

[56] References Cited
UNITED STATES PATENTS

| | | | |
|---|---|---|---|
| 2,228,268 | 1/1941 | Hansley | 260/586 A |
| 2,365,290 | 12/1944 | Price et al | 260/537 |
| 2,656,390 | 10/1953 | Stoll | 260/586 A |
| 3,254,127 | 5/1966 | Schnider | 260/586 A |
| 3,383,404 | 5/1968 | Miller et al. | 260/485 R |
| 3,796,630 | 3/1974 | Wegner | 195/28 R |
| 3,823,070 | 7/1974 | Minato et al | 195/28 R |

OTHER PUBLICATIONS

Kester et al., "Diterminal Oxidation of Long Chain Alkanes by Bacteria" J. Bacteriology, vol. 85, pp. 859–868.

*Primary Examiner*—A. Louis Monacell
*Assistant Examiner*—R. B. Penland

[57] ABSTRACT

A method of producing a macrocyclic ketone by microbially oxidizing a n-paraffin to produce a hydroxy acid, oxidizing the hydroxy acid to produce a diacid, esterifying the diacid to produce a diester, condensing the diester to produce a cyclic hydroxy ketone and reducing the cyclic hydroxy ketone to produce the macrocyclic ketone.

9 Claims, No Drawings

OXIDATION OF HYDROXY ACIDS PRODUCED FROM BACTERIAL OXIDATION OF PARAFFINS

This invention relates to the oxidation of hydroxy acids produced from bacterial oxidation of paraffins.

In one of its more specific aspects, this invention relates to the production of macrocyclic ketones from diesters of hydroxy acids by means of an acyloin condensation reaction scheme.

In another of its more specific aspects, this invention pertains to the oxidation of hydroxy acids contained in fermentation liquors also containing dicrboxylic acids having from 14 to about 22 carbon atoms per molecule, to produce macrocyclic ketones which are usable as odorants, particularly in the perfume industry.

The production of dicarboxylic acids having from about 6 to about 22 carbon atoms produced from $C_6$–$C_{22}$ n-paraffins by microbial oxidation in cultures containing the yeast *Torulopsis bombicola*, N. Sp., PRL319-67, obtainable from Prairie Regional Laboratory, National Research Council of Canada, Saskatoon, Saskatchewan, is well known.

Similarly it is well known to produce dicarboxylic acids from n-paraffins by use of yeast mutants of *Torulopsis bombicola*. Such mutants are available from the United States Department of Agriculture, Agricultural Research Center, North Central Region, Northern Regional Research Laboratory, Peoria, Ill. as strain NRRL-Y-7569 and NRRL-Y-7570.

The fermentation of n-paraffins by microbal oxidation employing such yeasts have now been found to produce fermentation liquors containing dicarboxylic acids and, in addition, hydroxy acids, e.g., omega-hydroxycarboxylic acids. It is toward the latter, which are generally considered to be impurities in the fermentation liquor, that this invention is directed.

According to the method of this invention hydroxy acids produced by the bacterial oxidation of paraffins are oxidized to the diacid, the diacid is esterified, the diester is subjected to cyclization to produce a cyclic hydroxy ketone and the hydroxy ketone is reduced to produce a cyclic saturated ketone.

Alternately, the cyclic hydroxy ketone can be converted directly to a cyclic unsaturated ketone which is then selectively hydrogenated to the cyclic saturated ketone.

In the method of this invention, the fermentor liquor or effluent is treated, as hereinafter described, to remove cell residues and other insoluble materials and to produce a fermentation product containing the hydroxy acids and containing from about 3 to about 30, and preferably from about 10 to about 25, weight percent of the crude dicarboxylic acids.

Suitable oxidizing agents for treatment of the hydroxy acids contained in these crude dicarboxylic acids according to this invention are those known in the art for the conversion of primary alcohols to carboxylic acids.

For example, nitric acid (40–100% $HNO_3$) at 40–100° C. in the presence, or absence, of an oxidation catalyst is a suitable oxidizing agent. The oxidation catalyst, if employed, is usually a compound of vanadium and can be used with or without an added cocatalyst such as copper. Ceric nitrate, with or without copper, is also a suitable oxidation catalyst for use with nitric acid.

Another suitable oxidizing system is dinitrogen tetroxide ($N_2O_4$) employed at temperatures of about −10° to about −20° C. for up to 50 hours. This reagent can be used in the presence of a paraffinic diluent such as n-heptane.

Other suitable oxidizing agents are potassium dichromate and sodium dichromate, individually or in combination, in sulfuric acid or in a mixture of sulfuric and acetic acids. Either of the dichromates is usually employed at 10°–80° C. for about 2–8 hours.

Aqueous sodium hydroxide or soda-lime under pressure at 200°–250° C. can also be employed to accomplish the desired oxidation step.

The use of air in the presence of potassium hydroxide in hexamethyl phosphoramide is also a suitable oxidizing system for use in the instant invention.

Potassium permanganate in basic aqueous media at 0°–50° C. for up to 20 hours can also be employed as the oxidizing agent for use in the invention.

The hydroxy acids are treated with an oxidizing agent to produce diacids and these diacids, combined with those diacids originally in the fermentor liquid product, can be covered by cooling the reaction mixture to precipitate the diacids, if not already insoluble in the reaction medium, and then filtering the diacids from the mixture. The recovered diacids are then washed thoroughly to remove traces of the oxidation reaction system. Usually this washing will result in a color-free (white) diacid product. Occasionally, it may be desirable to use a preliminary washing step employing a dilute solution of a reducing agent in order to destroy any occluded oxidizing agent remaining with the recovered diacids.

The recovered dicarboxylic acids are then esterified with a lower alkanol, e.g., methanol or ethanol to form diesters. The diesters can be treated with a sodium dispersion to perform the cyclization (intramolecular acyloin condensation) to the cyclic α-hydroxyketones (cyclic acyloin) which can be reduced directly to the cyclic ketones by hydrogen iodide or zinc and hydrochloric acid. Alternatively, the cyclic acyloins can be dehydrated to the cyclic unsaturated ketones which can be selectively hydrogenated to the cyclic saturated ketone.

The above sequence of steps can be represented by the chemical reactions shown schematically below:

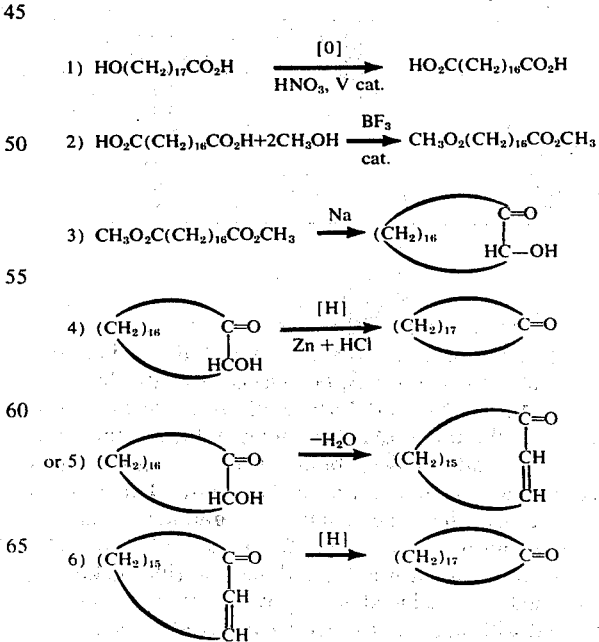

The individual steps of esterification of the diacids, forming the cyclic acyloins from the diesters, and obtaining the cyclic ketones from said cyclic acyloins are well known in the art although they are described in detail in the following examples. However, the benefits of the instant invention are observed in at least two aspects of this sequence of reaction steps.

First, the yield of diester is improved when the crude diacid mixture is treated with an oxidizing agent according to this invention prior to the esterification reaction. Second, the acyloin condensation reaction requires significantly less time if the diester reactant is prepared from the crude diacid mixture treated with an oxidizing agent according to this invention than if the diester is prepared from the untreated crude diacid. These factors, as well as the best mode of practicing the invention are demonstrated by the following examples.

EXAMPLE I (Control)

A. Diacid — Fourteen fermentations were carried out aerobically with n-octadecane as the primary source of carbon according to the following general procedure.

A sucrose-containing nutrient was prepared by dissolving the following ingredients in sufficient distilled water to give a liter of solution.

| Component | Grams Per Liter |
| --- | --- |
| Sucrose | 40 |
| Commercial Yeast Extract | 5 |
| Urea | 1 |
| $KH_2PO_4$ | 1 |
| $MgSO_4.7H_2O$ | 3 |
| Mineral Solution | 1 ml |

The mineral solution employed above was prepared by adding the following materials, in the quantities shown, to water to form 1 liter of solution.

| Component | Grams Per Liter of Solution |
| --- | --- |
| $CuSO_4.5H_2O$ | 0.06 |
| KI | 0.08 |
| $MnSO_4.H_2O$ | 0.30 |
| $NaMoO_4.2H_2O$ | 0.20 |
| $H_3BO_3$ | 0.02 |
| $ZnSO_4.7H_2O$ | 2.0 |
| $FeCl_3.6H_2O$ | 4.8 |

A 4 liter sample of the sucrose-containing medium was then innoculated with 500 ml of 5-day old culture of a mutant *Torulopsis bombicola*, specifically with strain NRRL-Y-7570. Fifty g of n-octadecane were added to the mixture and the temperature of the composite was adjusted to about 30° C. The mixture was agitated and air was introduced at a rate of about 0.10 volume per minute per volume of fermentation liquor. Fermentation was contained for about 137 hours. The fermentor effluent was filtered and the filter cake was air dried and reduced to a powder. It was then extracted with acetone to recover the crude diacid.

The acetone extraction was conducted for about 2 hours using about 2 liters of acetone per about 200 grams of dried cell mixture. The extract was filtered to remove cell residues and other insoluble materials. The filtrate was condensed until a slurry was obtained and the slurry was diluted with n-hexane. The resulting mixture was cooled with ice water to precipitate the extracted crude diacid containing hydroxy acid. This crude acid mixture was dried.

B. Esterification — A mixture of crude diacids containing hydroxy acids, such as that obtained by the acetone extraction procedures, generally described above, was esterified with ethanol according to the procedures given below. The crude diacids were comprised principally of octadecanedioic acid.

A 2-liter flask equipped with condenser and water take-off means was charged with 85.3 g (0.27 mols) of the diacid mixture, 600 ml toluene, 60 ml (1.0 mol) absolute ethanol and 1.5 ml concentrated sulfuric acid. This mixture was refluxed for about 30 hours and about 36 ml of a mixture of water and ethanol was recovered from the reaction mixture during this period. The reaction mixture was then washed with water and the organic phase separated and condensed by removing the toluene under vacuum. Fractional distillation of the condensed organic phase under vacuum then recovered 56.1 g (0.15 mol) of the diester for a 56 mole percent yield.

C. Acyloin Condensation — A 2-liter Morton flask equipped with heating and stirring means, thermometer, reflux condenser, nitrogen gas inlet and addition funnel was charged with 800 ml of xylene and 6.5 g (0.283 g atoms) of sodium. A dispersion of the sodium was formed by heating and vigorous stirring. To the stirred and heated sodium dispersion was slowly added 24.5 g (0.066 mols) of the diethyl ester of octadecanedioic acid prepared in the manner as described above (B.). Heating and stirring of the reaction mixture was carried out for a total of about 12.5 hours. However, visible particles of sodium metal remained thereafter. Treatment of the reaction mixture with ethanol and then water produced a suspension that was difficult to separate into aqueous and organic phases. Removal of solids by filtration appeared to aid phase separation. The organic phase was separated, condensed, then fractionally distilled to provide 8.5 grams of product comprising the cyclic acyloin, α-hydroxycyclooctadecanone, for a yield of 46% based on the diester.

D. Reduction of Acyloin — The cyclic acyloin prepared above was reduced to the cyclic ketone, cyclooctadecanone, by the combination of zinc and hydrochloric acid in the following manner. A 300 ml flask equipped with heating and stirring means, reflux condenser, thermometer and gas inlet through a fritted glass dispersion tube was charged with 6.5 g (0.023 mols) of the cyclic acyloin, 225 ml dioxane and 10 g of powdered zinc. The reaction mixture was heated to 95°–110° C. and HCl gas bubbled through the mixture for about 3 hours. Two grams of zinc dust was added and the reaction continued for 2 more hours. The reaction was then suspended overnight and resumed again for an 8 hour period with an additional 2 grams of zinc dust being added at the beginning of the last reaction period. Upon termination of the reaction, the dioxane was removed under vacuum and the residue washed with water and extracted with n-pentane. The pentane extract was dried over $MgSO_4$, filtered and the n-pentane removed. The residue (13.0 g) was fractionally distilled to provide 4.2 g of the cyclic ketone, cyclooctadecanone.

EXAMPLE II (INVENTION)

A. Diacid — Acetone extraction of fermentor effluent as described in Example I, Part A, provided a crude diacid and hydroxy acid mixture comprising octadecanedioic acid for use in Example II.

B. Oxidation of the Crude Diacid Mixture — A run employing 100 g (0.60 mol) of the crude diacid containing the hydroxy acid was carried out in the manner described below. A 1-liter, three-necked, flask equipped with heating and stirring means, reflux condenser, thermometer, and powder addition funnel was charged with 300 ml concentrated nitric acid (70% by wt. $HNO_3$), 0.2 g ammonium vanadate dissolved in about 5 ml concentrated $HNO_3$, and 0.3 g copper shot. The crude diacid mixture was added to the stirred mixture in small portions over a period of about 1.25 hours while the temperature was maintained at 55°–60° C. Several grams of copper shot and 2 - 100 ml portions of concentrated $HNO_3$ were also added during this period. After all the crude diacid mixture had been added, the temperature of the reaction mixture was increased slowly to about 90° C. over a period of about 3.5 hours while stirring was continued. The mixture was then cooled and filtered to recover the diacid on the filter. The diacid was stirred vigorously with water at about 40° C. The mixture was cooled, filtered, and the washed diacid dried to provide 99.5 grams of diacid treated according to the instant invention.

C. Esterification — A 1-liter flask equipped with heating means, water take-off means (Dean-Stark trap), reflux condenser and thermometer was charged with 97 g (0.31 mol) of the treated diacid, 600 ml toluene, 65 ml ethanol and 1.5 ml concentrated sulfuric acid. The mixture was refluxed about 13 hours during which time 76 ml of a water-ethanol mixture was recovered from the reaction mixture. The residual reaction mixture was washed twice with water and the organic phase recovered and condensed by removal of toluene under vacuum. Fractional distillation under vacuum then provided 88.9 g (0.24 mol) of the diester for a 77 mole percent yield.

It can be seen that the yield of desired diester in the esterification step, above, is significantly higher than that achieved in Example I which employed the crude diacid without the oxidation treatment of this invention.

D. Acyloin Condensation — A 3-liter Morton flask equipped with heating and stirring means, thermometer, reflux condenser, nitrogen gas inlet and addition funnel was charged with 2500 ml xylene and 20.0 g (0.88 g atoms) of sodium. A dispersion of the sodium was formed by heating and stirring. The diester prepared in step (C.), above, (81.5 g, 0.22 mols) dissolved in 100 ml xylene was slowly added over a two-hour period to the stirred and heated sodium dispersion. After about 1.5 hours of additional stirring with heating, no sodium metal particles could be seen. Treatment of the reaction mixture, which had been cooled from 100° C. to about 70° C., with ethanol (250 ml) and washing the mixture with 400 ml water gave an emulsion with some solid material. This mixture was filtered and the organic phase separated from the aqueous phase. The organic phase was then stripped of xylene and other volatiles under vacuum to give a residue of 52.5 g crude acyloin. Fractional distillation of 49.0 g of the above residue gave 27.2 g of product comprising the cyclic acyloin, α-hydroxycyclooctadecanone, for a yield of 44% based on the diester.

It should be noted that the yield of distilled acyloin in this example is essentially the same as that shown in Example I, part C. The advantage of the method of the present invention over the conrol run in the acyloin formation step lies in the much greater rapidity of sodium metal consumption thereby providing a distinct economic advantage in the shorter reaction time for the process of the invention.

E. Reduction of Acyloin — A 500 ml flask equipped with heating means and flux condenser was charged with 25 g (0.087 mols) of the acyloin from step D, above, 90 g of HI as a 37% by wt. solution in water, and 150 ml glacial acetic acid. The mixture was heated at reflux for 1.5 hours. The reaction mixture was added to a vigorously stirred aqueous solution of NaOH (112 g) and sodium bisulfite (25 g) in water (750 ml). The organic layer was separated and the aqueous layer was extracted with 200 ml ether. The ether extract was combined with the organic layer and the combination was stripped of volatile materials on a rotary evaporator. The residue was washed with an aqueous solution (50 ml) containing 1 g NaOH and about 3 g $NaHSO_3$. The aqueous wash was extracted with 200 ml ether which was combined with the organic layer and stripped of volatiles as before. The residue was washed again with aqueous $NaHCO_3$ until basic to litmus. The aqueous wash was extracted with ether and the ether extract combined with the organic layer and stripped of volatiles as before to give 26 g of residue. Fractional distillation under vacuum of 23.5 g of the above residue gave 12.8 g of product cyclooctadecanone.

EXAMPLE III (INVENTION)

A. Diacid — Acetone extraction of fermentor effluent as described in Example I, part A, was employed to provide a crude diacid and hydroxy acid mixture comprising octadecanedioic acid for use in Example III.

B. Oxidation of the Crude Diacid Mixture — A 5-liter flask equipped with heating and stirring means, reflux condenser, thermometer, and powder-addition funnel was employed as the reaction vessel. A solution of 2.0 g of ammonium metavanadate in a mixture of 20 ml concentrated $HNO_3$ and 20 ml water was prepared. The reaction vessel was charged with 30 ml of the above solution, 1 liter of concentrated $HNO_3$ and 2.4 g of copper. The temperature of the stirred mixture was raised to 55° C. and 419 g (1.33 mols) of the crude diacid, obtained as described above, was added in small portions over a period of about 1 hour. On completion of the diacid addition, 400 ml of concentrated $HNO_3$, the remaining 10 ml of the ammonium metavanadate solution, and 0.6 g of copper were added to the reaction mixture. After about 0.5 hour, an additional 200 ml of concentrated $HNO_3$ was added to the mixture. The temperature of the mixture was slowly raised to 90° C. while stirring over a period of about 3 hours. The mixture was then cooled to 25° C. and filtered through a fritted glass funnel. The filtrate was discarded and the recovered diacid was washed with about 2 liters of water and then dried. In order to more effectively remove residual $HNO_3$, the diacid was washed twice with about 1 liter of water by use of rapid mixing in a Waring Blendor for 3–4 minutes. This washed product was dried in a vacuum oven for 5 hours at 65° C. The material (402 g) was then mixed with 1500 ml n-hexane in a Waring Blendor for 3–4 minutes and then filtered. The recovered diacid (354 g), when analyzed by gasliquid phase chromatography (GLC), contained about 8 percent monoacid (octadecanoic acid) while the material extracted by n-hexane was comprised of about 50 percent octadecanoic acid, 27 percent octadecane, and small amounts of dicarboxylic acids and other unidentified compounds.

C. Esterification — A 3-liter Morton flask equipped with heating and stirring means, thermometer and flux condenser was charged with 346 g (1.1 mol) of the octadecanedioic acid obtained in part B above, 500 ml of a 10 weight percent solution of $BF_3$ in methanol, and 1700 ml of anhydrous methanol. The temperature of the stirred reaction mixture was raised slowly over a 1 hour period to reflux (66° C.) and maintained there for 1.5 hours. Excess methanol was removed by distillation at atmospheric pressure followed by use of a rotary evaporator under vacuum. Ether was added to the residue and the resulting ether solution was washed twice with water, once with an aqueous sodium bicarbonate solution, and twice again with water. The ether solution was stripped of ether by use of a rotary evaporator under vacuum. The residue was fractionally distilled under vacuum to obtain as overhead product, 307 g and there remained 55 g distillation flask residue. Of the overhead product, five of the total of 12 fractions obtained comprised dimethyl esters of diacids having 16, 17, and 18 carbon atoms per molecule with the eight of these five fractions totaling 217 g. Of the five fractions, one fraction (No. 11) which weighed 100 g, was comprised of 96 weight percent dimethyl ester of octadecanedioic acid and 4 weight percent dimethyl ester of heptadecanedioic acid.

Yield calculations based only on the weight of the five fractions described above and the total weight of starting diacid gave a mole percent yield of about 66 percent for the combined diesters of the $C_{16}$, $C_{17}$ and $C_{18}$ diacids.

D. Acyloin Condensation — A 5-liter Morton flask equipped with stirring and heating means, condenser, dropping funnel and nitrogen gas bleed was charged with 3.1 liters of dry toluene and 25.0 g (1.08 g atoms) of sodium metal. The mixture was heated to 95°–98° C. and vigorous stirring started which produced a sodium dispersion. The temperature was increased to about 110° C. at which time the addition of a solution of 78.6 g (0.231 mols) of diester (fraction No. 11 described in part E, above) in 50 ml dry toluene was begun. Addition of the diester was completed in about 2 hours and stirring as continued for an additional 0.5 hour. The reaction mixture was cooled to about 25° C. and 300 ml methanol added slowly followed by addition of 125 ml water. No evidence of incomplete sodium metal consumption was noted. The organic phase was separated and washed with portions of water until the wash water was no longer basic to pH paper. The wate phase was extracted with ether and the ether extract combined with the organic phase. The combined organic phase was then concentrated by use of a rotary evaporator under vacuum to provide 56 g of viscous yellow residue as the crude acyloin.

E. Reduction of Acyloin — A 2-liter Morton flask equipped with heating means and reflux condenser was charged with 56 g of crude acyloin obtained in part D, above, 600 ml of glacial acetic acid. To this mixture was added 224 g (152 ml) of a 47 weight percent solution of HI in water over about a 10 minute period. The reaction mixture was heated for about two hours under reflux conditions. The reaction mixture was cooled to about 23° C. and added to a stirred solution of 420 g NaOH and 104 g $NaHSO_3$ in 2 liters of water. This mixture was then extracted with 1 liter of ether, then with two 500 ml portions of ether. The combined ether extracts were washed with aqueous NaOH, aqueous $NaHSO_3$ and finally twice with water. The ether solution was dried over anhydrous $MgSO_4$ and filtered. The filtrate was condensed by stripping off the ether using a rotary evaporator under vacuum. A residue of 50.4 g was obtained. Fractional distillation of 46.3 g of this residue provided 29.7 g of a cyclic ketone product comprising cyclooctadecanone which represents a 49 percent yield based on the diester intermediate.

It is to be understood that the method of this invention is applicable to hydroxy acids in the absence of any substantial quantity of diacids. Further, this invention is applicable to any microbial oxidation which produces hydroxy acids.

It will be evident from the foregoing that various modifications can be made to the method of this invention. Such, however, are considered to be within the scope of the invention.

What is claimed is:
1. A method of producing a macrocyclic ketone which comprises:
   a. microbially oxidizing a n-paraffin containing from about 6 to about 22 carbon atoms to produce a fermentation liquor containing a mixture of a diacid and a hydroxy acid;
   b. separating said mixture of said diacid and said hydroxy acid from said fermentation liquor;
   c. subjecting said mixture to oxidizing conditions so as to oxidize said hyroxy acid to produce additional diacid;
   d. esterifying said diacid to produce a diester;
   e. condensing intramolecularly said diester to produce a cyclic hydroxy ketone; and,
   f. reducing said cyclic hydroxy ketone to produce a macrocyclic ketone.

2. The method of claim 1 in which said hydroxy acid is oxidized by contacting said hydroxy acid with a material selected from the group consisting of nitric acid, dinitrogen tetroxide, potassium dichromate, sodium dichromate, sodium hydroxide, soda lime, potassium hydroxide, air, and potassium permanganate.

3. The method of claim 1 in which said diacid is contacted with a lower alkanol to produce said diester.

4. The method of claim 1 in which said diester is contacted with a sodium dispersion to intramolecularly condense said diester.

5. The method of claim 1 in which said cyclic hydroxy ketone is contacted with hydrogen iodide or zinc and hydrochloric acid to reduce said cyclic hydroxy ketone.

6. The method of claim 1 in which said cyclic hydroxy ketone is converted to a cyclic unsaturated ketone and said cyclic unsaturated ketone is hydrogenated to produce said macrocyclic ketone.

7. The method of claim 1 in which hydroxy acid is oxidized by contacting said hydroxy acid with nitric acid, said diacid is esterfied by contacting with ethanol and said diester is intramolecularly condensed by contacting said diester with sodium dispersed in xylene.

8. The method of claim 1 in which said mixture is separated by filtering said fermentation liquor to recover a solid and said solid is contacted with a solvent to extract said mixture of dacid and hydroxy acid from said solid.

9. The method of claim 1 in which said n-paraffin is n-octadecane and said n-octadecane is microbially oxidized by contacting said n-octadecane with the yeast *Torulopsis bombicola* or a mutant of said yeast.

* * * * *